United States Patent [19]

Yanney

[11] 4,259,076
[45] Mar. 31, 1981

[54] METHOD AND APPARATUS FOR CONNECTING AN ARTIFICIAL TOOTH PORTION TO A DENTIN PORTION

[76] Inventor: James F. M. Yanney, 8230 Elizabeth Dr., Lincoln, Nebr. 68505

[21] Appl. No.: 82,441

[22] Filed: Oct. 9, 1979

[51] Int. Cl.³ .................................................. A61C 5/04
[52] U.S. Cl. ...................................................... 433/225
[58] Field of Search ............... 433/225, 220, 221, 173; 128/92 C; 3/1.9

[56] References Cited

U.S. PATENT DOCUMENTS

| 756,506 | 4/1904 | Kidder | 433/221 |
|---|---|---|---|
| 1,100,252 | 6/1914 | O'Neill | 85/21 |
| 3,740,851 | 6/1973 | Weissman | 433/225 |

*Primary Examiner*—Robert Peshock
*Attorney, Agent, or Firm*—Henderson & Sturm

[57] ABSTRACT

A method and apparatus for connecting an artificial tooth portion to a dentin portion utilizing an elongated member having a generally circular cross sectional shape one one end portion thereof and barbs attached to and disposed around the periphery of the one end portion thereof for directly engaging the dentin portion within the bore. The method includes the steps of removing a portion of a tooth down to the dentin portion, forming an opening having interior walls in the dentin portion of the tooth which is slightly larger in diameter than the diameter of the circular cross sectional one end portion of the elongated member, forcing the one end portion of the elongated member into the opening whereby the barbs are tightly wedged against the interior walls thereof and whereby the other end of the elongated member extends out of the opening and attaching the artificial tooth portion to the other end of the elongated member and in abutment with the dentin portion of the tooth whereby the artificial tooth portion is held in place with respect to the tooth.

11 Claims, 5 Drawing Figures

METHOD AND APPARATUS FOR CONNECTING AN ARTIFICIAL TOOTH PORTION TO A DENTIN PORTION

BACKGROUND OF THE INVENTION

The present invention relates generally to a method and apparatus for rebuilding teeth, and more specifically to a novel retention pin and a method for using it.

In the dentistry field it is of course, common to rebuild a portion of a tooth. When the tooth portion being rebuilt cannot be shaped such that the tooth itself will hold a filling or other artificial tooth portion, then it becomes necessary to use some other method and apparatus for attaching such artificial tooth portion to such tooth. One method in common usage is the use of a retention pin. In using such a retention pin, normally the portion of the tooth which needs to be replaced is ground off down to the dentin portion. Then a very small hole is bored into the dentin portion of the tooth. A small retention pin having threads around the periphery thereof is then either manually or mechanically rotated such that it is screwed down into the hole in the dentin. A portion of such retention pin would then extend outwardly from the dentin portion and would also have threads thereon for facilitating anchoring of an artificial tooth portion thereto. The artificial tooth portion would then be formed over and around such retention pin so that when this artificial tooth portion hardened, it would be secured to the dentin portion of the tooth by the retention pin.

While this has been a generally well accepted procedure, it has been discovered that this procedure causes crazing of the dentin at the point at which the pin connects to the dentin portion of the tooth. In an article beginning on page 941 of J Dent Res in the July-August 1974 issue, vol. 53, no. 4, by Chan et al., the problem was researched and discussed with a conclusion that the wedging of such self-threading retention pins causes these cracks in the dentin portion, thereby eventually causing the connection to fail or deterioration of the tooth to occur.

In the dentistry field, it is also well known to attach tooth portions together by the use of some sort of retention structure, such as a pin which has one portion cemented to a tooth and the other portion having an artificial section which is formed around such retention member. One patent, U.S. Pat. No. 2,721,387 issued to Ashuckian, shows a very complicated structure for attaching an artificial tooth to a person's jaw and having a plurality of barbs thereon for allowing the jaw portion to grow therearound to make a connection. U.S. Pat. Nos. 756,506 to Kidder, 1,517,500 to Fredericks and 4,139,943 to Dragan are illustrations of the prior art showing barbed pins or the like for connecting tooth portions together. This prior art does not, however, recognize the dentinal crazing problem referred to above and does not provide a structure or method for connecting the dentin portion of a tooth to an artificial portion.

Consequently, there is a definite need for structures and methods for overcoming the above-identified problem.

SUMMARY OF THE INVENTION

The present invention relates to a method and apparatus for connecting an artificial tooth portion to a dentin portion utilizing an elongated member having a generally circular cross sectional shape on one end portion thereof and barbs attached to and disposed around the periphery of the one end portion thereof for directly engaging the dentin portion within the bore. The method includes the steps of removing a portion of a tooth down to the dentin portion, forming an opening having interior walls in the dentin portion of the tooth which is slightly larger in diameter than the diameter of the circular cross sectional one end portion of the elongated member, forcing the one end portion of the elongated member into the opening whereby the barbs are tightly wedged against the interior walls thereof and whereby the other end of the elongated member extends out of the opening and attaching the artificial tooth portion to the other end of the elongated member and in abutment with the dentin portion of the tooth whereby the artificial tooth portion is held in place with respect to the tooth.

An object of the present invention is to provide an improved method and apparatus for installing a retention pin in the dentin portion of a tooth for attaching an artificial tooth portion thereto.

Another object of the invention is to provide a retention pin which will not cause crazing of the dentin portion of a tooth.

A further object of the invention is to provide a retention pin which can be easily and quickly inserted into the dentin portion of a tooth without the disadvantage of the prior art of having to rotate it in a self-threading manner.

Other objects, advantages and novel features of the present invention will become apparent from the following detailed description thereof.

DESCRIPTION OF THE PREFERRED EMBODIMENT

Figure 1:
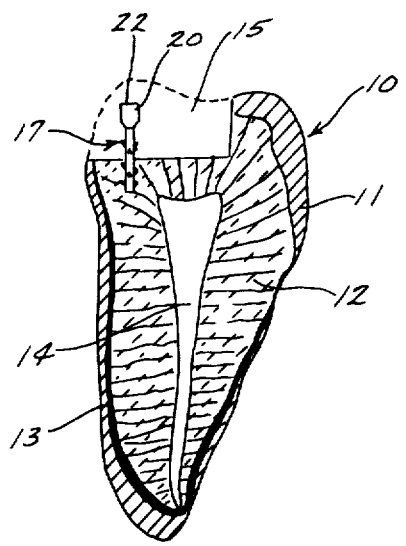
FIG. 1 shows a cross sectional view of a tooth and showing a possible position for a retention pin of the present invention.

Referring now to the drawings, wherein like reference numerals designate identical or corresponding parts throughout the several views, FIG. 1 shows a cross sectional view of a mandibular right permanent second molar 10 having an enamel portion 11, a dentin portion 12, a cementum portion 13 and a pulp portion 14. The upper portion of the tooth 10 has a section 15 thereof which has been removed and is therefore indicated in dashed lines to show what has been removed and also shows the shape of the artificial portion which will be inserted in its place. Once the portion 15 of the tooth has been removed by conventional dental procedures down to the dentin portion 12, a small hole 16 is drilled into the dentin portion 12 as can best be seen in FIG. 2.

A retention pin 17 is comprised of an elongated cylindrical member 18 having a plurality of barbs 19 disposed around the periphery thereof and along the length thereof.

Figure 2:
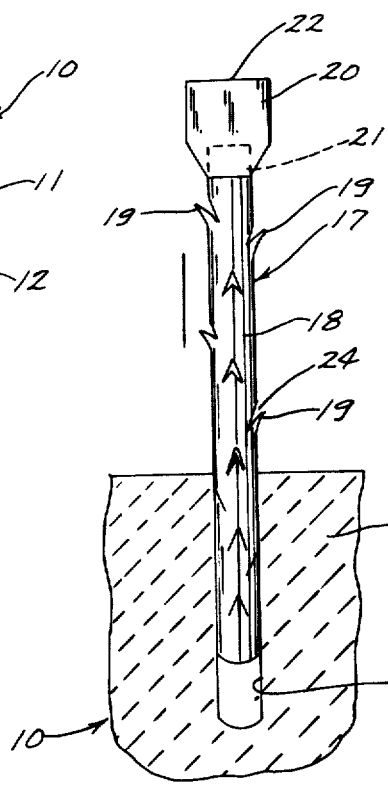
FIG. 2 shows an enlarged cross sectional view of the dentin portion of a tooth and showing an opening in the dentin portion and the retention pin of the present invention being inserted therein.
Figure 3:
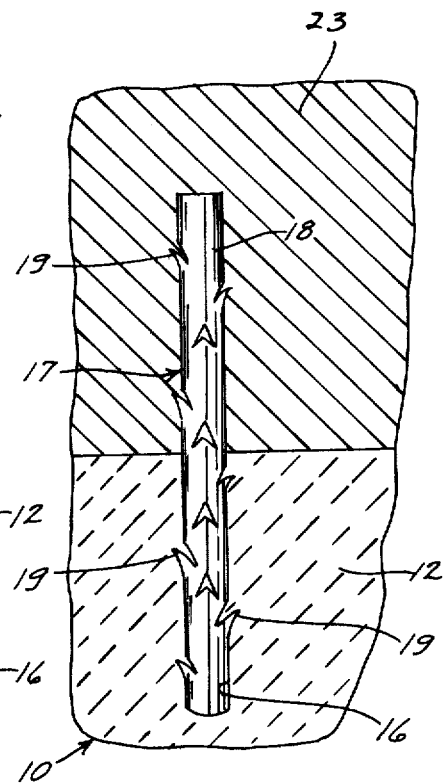
FIG. 3 shows the retention pin of the present invention being installed in the dentin portion of a tooth and also having an artificial tooth portion attached thereto.

Installation of the retention pin 17 is facilitated by the use of a removable cap portion 20 having an opening 21 in the bottom portion thereof as viewed in FIG. 2. This cap 20 provides a larger surface 22 for applying pressure to the pin 17 for facilitating pushing it into the opening 16 in the dentin 12. As the pin 17 is pushed into the opening 16, the barbs 19 are caused to be moved inwardly back into the space 24 provided in the pin 18 as can best be seen in FIG. 2. The size of the opening 16 should be approximately the same size as the pin 18 although, perhaps slightly larger than the diameter of such hole 16 in some instances, but in no event should it be so large that the barbs 19 would not be forced inwardly when the pin 18 is forced into the opening 16. Upon insertion of the pin 17, the barbs 19 will flex closed following the walls of the prepared opening 16 in the dentin until the pin is fully seated and at the bottom of the opening 16. Relief of the pressure from insertion on the pin 17 will allow the barbs to re-expand to some extent. These barbs 19 will continue to expand and create more of a facility to provide retention upon the exertion of any forces thereon, such as a force towards removal thereof.

As an example only, the retention pin 17 could be approximately 4 mm. in length with 2 mm. being disposed within the dentin portion of the tooth and 2 mm. extending into the amalgam or artificial tooth portion 23. The diameter of the pin 18 can, of course, vary considerably, but a diameter of 0.017 inches has been determined to be an optimum size.

Once the pin 17 is fully inserted into the opening or channel 16, then the amalgam 23 is formed over the top of the pin 18, noting, of course, that the removable member 20 is removed. This amalgam 23 is then shaped again to assume approximately the same shape that the tooth was originally, for example, the shape shown by the space 15 between the dentin portion 12 and the dashed lines of FIG. 1. Once this is done, the method of the present invention is complete and the amalgam portion 23 is secured to the dentin portion 12 of the tooth.

Figure 4:
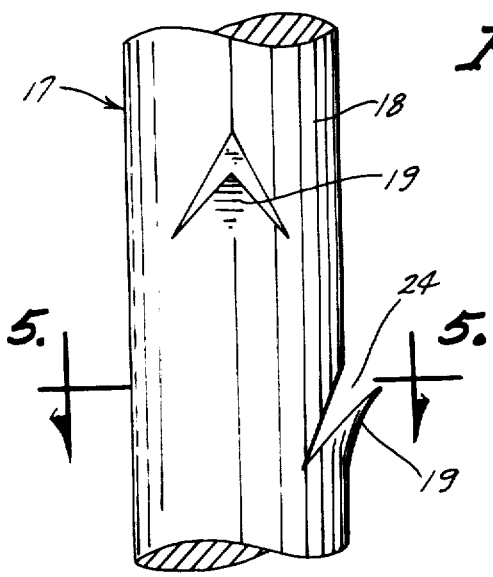
FIG. 4 is an enlarged side elevational view of the retention pin of the present invention showing the barb portion in detail.
Figure 5:
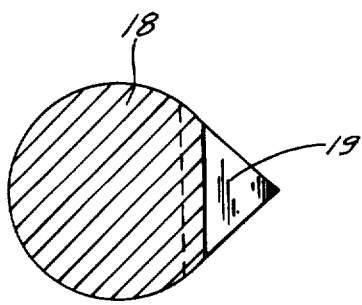
FIG. 5 is a cross sectional view taken along line 5—5 of FIG. 4.

Referring to FIGS. 4 and 5, it is noted that the barbs 19 are formed by cutting into the sidewall of the cylindrical pin 18 and then pushing the extreme outer end or free end of the barb 19 outwardly.

It is therefore believed to be clear that the preferred embodiment shown and described does indeed accomplish all of the objects set forth above. Obviously, many modifications and variations of the present invention are possible in light of the above teachings. It is therefore to be understood that, within the scope of the appended claims, the invention may be practiced otherwise than as specifically disclosed herein.

I claim:

1. Apparatus for connecting an artificial replacement tooth portion to a dentin portion of a tooth having a cylindrically shaped bore therein comprising:
   an elongated cylindrical member having a generally circular cross sectional shape
   barb means attached to, formed on, and disposed around the periphery of one end portion thereof for directly engaging the dentin portion within said bore; and
   a smooth cylindrical surface on the other end portion dimensioned to releasably engage a force receiving means in the form of an enlarged hollow cap member, which has an external force applied thereto, to drive the apparatus into the cylindrically shaped bore.

2. The apparatus of claim 1 wherein said barb means comprises a plurality of barb members connected at a base portion on one end thereof to said elongated members and extending radially outwardly from the periphery of said elongated member to a free end thereof, said barb members being wider at the base portion thereof than at the free end thereof whereby the free end can readily conform to the bore in the dentin.

3. The apparatus of claim 2 wherein the base portion of each respective barb member extends farther into the bore than each respective free end portion thereby tending to anchor said elongated member into said bore.

4. The apparatus of claim 1 wherein said artificial tooth portion is disposed around the other end portion of said elongated member and said other end portion of said elongated member includes anchoring means for preventing relative movement of said artificial replacement portion with respect to said elongated portion.

5. The apparatus of claim 4 wherein said anchoring means comprises a plurality of barb members attached to and disposed around the periphery of said other end of said elongated member.

6. A method for connecting an artificial tooth portion to a dentin portion utilizing an elongated member having a generally circular cross sectional shape on one end portion thereof and barb means attached to and disposed around the periphery of said one end portion thereof for directly engaging the dentin portion within said bore, said method comprising:
   removing a portion of a tooth down to the dentin portion thereof;
   forming an opening having interior walls in the dentin portion of the tooth which is slightly larger in diameter than the diameter of said circular cross sectional one end portion of the elongated member;
   forcing said one end portion of said elongated member into said opening whereby said barb means are tightly wedged against the interior walls thereof and whereby the other end of the elongated member extends out of said opening; and
   attaching said artificial tooth portion to said other end of the elongated member and in abutment with the dentin portion of the tooth whereby said artificial tooth portion is held in place with respect to said tooth.

7. The method of claim 6 wherein said artificial tooth portion is attached to the other end of the elongated member by forming it around said other end in a plastic condition and allowing it to harden to a solid condition.

8. A method for connecting an artificial tooth portion to a dentin portion utilizing an elongated member having a generally circular cross sectional shape on one end portion thereof; and
   barb means attached to and disposed around the periphery of said one end portion thereof for directly engaging the dentin portion within said bore, said barb means comprising a plurality of barb members connected at a base portion on one end thereof to said elongated members and extending radially outwardly from the periphery of said elongated member to a free end thereof, said barb members being wider at the base portion thereof than at the free end thereof whereby the free end can readily conform to the bore in the dentin, the other end of said elongated member including anchoring means for preventing relative movement of said artificial replacement portion with respect to said elongated portion, said method comprising:

removing a portion of a tooth down to the dentin portion thereof;

forming an opening having interior walls in the dentin portion of the tooth which is slightly larger in diameter than the diameter of said circular cross sectional one end portion of the elongated member;

forcing said one end portion of said elongated member into said opening whereby said barb means are tightly wedged against the interior walls thereof and whereby the other end of the elongated member extends out of said opening; and attaching said artificial tooth portion to said other end of the elongated member and in abutment with the dentin portion of the tooth whereby said artificial tooth portion is held in place with respect to said tooth.

9. The method of claim 8 wherein said artificial tooth portion is attached to the other end of the elongated member by forming it around said other end in a plastic condition and allowing it to harden to a solid condition.

10. A method for connecting an artificial tooth portion to a dentin portion utilizing an elongated member having a generally circular cross sectional shape on one end portion thereof and barb means attached to, formed on and disposed around the periphery of the other end portion thereof for directly engaging the dentin portion within said bore, wherein the said one end portion cooperates with a removable force receiving means in the form of a hollow cap member, said method comprising:

removing a portion of a tooth down to the dentin portion thereof;

forming an opening having interior walls in the dentin portion of the tooth which is slightly larger in diameter than the diameter of said circular cross sectional one end portion of the elongated member;

forcing said barbed end portion of said elongated member into said opening by applying force to said force receiving means whereby said barb means are tightly wedged against the interior walls thereof and whereby the said one end of the elongated member extends out of said opening; removing said force receiving means; and attaching said artificial tooth portion to said one end of the elongated member and in abutment with the dentin portion of the tooth whereby said artificial tooth portion is held in place with respect to said tooth.

11. The method of claim 10 wherein said artificial tooth portion is attached to the other end of the elongated member by forming it around said other end in a plastic condition and allowing it to harden to a solid condition.

* * * * *